(12) United States Patent
Gozani et al.

(10) Patent No.: US 7,749,171 B2
(45) Date of Patent: Jul. 6, 2010

(54) METHOD FOR AUTOMATED DETECTION OF A-WAVES

(75) Inventors: Shai N. Gozani, Brookline, MA (US); Xuan Kong, Acton, MA (US)

(73) Assignee: NeuroMetrix, Inc., Waltham, MA (US)

( * ) Notice: Subject to any disclaimer, the term of this patent is extended or adjusted under 35 U.S.C. 154(b) by 1277 days.

(21) Appl. No.: 11/076,789

(22) Filed: Mar. 9, 2005

(65) Prior Publication Data

US 2006/0020222 A1   Jan. 26, 2006

Related U.S. Application Data

(60) Provisional application No. 60/551,556, filed on Mar. 9, 2004.

(51) Int. Cl.
*A61B 5/05* (2006.01)

(52) U.S. Cl. .................................. 600/554; 600/546

(58) Field of Classification Search .............. 600/373, 600/378, 544–546, 554
See application file for complete search history.

(56) References Cited

U.S. PATENT DOCUMENTS

| | | | | |
|---|---|---|---|---|
| 5,491,627 A * | 2/1996 | Zhang et al. | ................ | 600/408 |
| 5,540,235 A | 7/1996 | Wilson | | |
| 6,132,386 A * | 10/2000 | Gozani et al. | ............... | 600/554 |
| 6,546,378 B1 * | 4/2003 | Cook | ......................... | 706/12 |
| 6,692,444 B2 | 2/2004 | Gozani et al. | | |
| 7,452,335 B2 | 11/2008 | Wells | | |

OTHER PUBLICATIONS

Bischoff et al., "Significance of A-waves recorded in routine motor nerve conduction studies," Clin Neurophys 1996; 101:528-533.*

* cited by examiner

*Primary Examiner*—Max Hindenburg
*Assistant Examiner*—Rene Towa
(74) *Attorney, Agent, or Firm*—Pandiscio & Pandiscio

(57) ABSTRACT

In one form of the present invention, there is provided a method for detecting an A-wave, the method comprising:
  applying a series of stimuli to a nerve;
  recording a series of late responses;
  creation of a feature space map from an ensemble of late responses;
  identification of clusters within the feature space that represent A-wave components;
  consolidation of A-wave components into a discrete collection of A-waves;
  removal of false positive A-waves; and
  extraction of A-wave characteristics.

In another form of the present invention, there is provided a system for detecting an A-wave comprising:
  a stimulation electrode;
  a stimulation circuit connected to the stimulation electrode for applying a series of stimuli to a nerve;
  a detection electrode;
  a detection circuit connected to the detection electrode; and
  an analyzer connected to the detection electrode and adapted to detect an A-wave by:
    recording a series of late responses detected by the detection circuit;
    creation of a feature space map from an ensemble of late responses;
    identification of clusters within the feature space map that represent A-wave components;
    consolidation of A-wave components into a discrete collection of A-waves;
    removal of false positive A-waves; and
    extraction of A-wave characteristics.

5 Claims, 4 Drawing Sheets

METHOD FOR AUTOMATED DETECTION OF A-WAVES

REFERENCE TO PENDING PRIOR PATENT APPLICATION

This patent application claims benefit of prior U.S. Provisional Patent Application Ser. No. 60/551,556, filed Mar. 9, 2004 by Shai Gozani et al. for METHOD FOR AUTOMATED DETECTION OF A-WAVES.

The above-identified patent application is hereby incorporated herein by reference.

BACKGROUND OF THE INVENTION

A nerve conduction study (NCS) is a diagnostic procedure whereby peripheral nerves are stimulated electrically and then bioelectrical potentials are recorded from the same nerve at a second location or from a muscle innervated by the activated nerve. A nerve conduction study often consists of early and late potentials. The former reflect direct conduction from the site of stimulation to the site of recording. Late potentials represent conduction from the site of stimulation antidromically towards the spinal cord—reflection along the way or in the spinal cord—and then conduction back down to the recording site.

The two most common types of late potentials associated with recording from a muscle innervated by the stimulated nerve are F-waves and A-waves. F-waves waves are highly variable waveforms that are caused by motor neuron back-firing and are generally recorded in all nerve conduction studies—whether pathology exists or not. A-waves, by contrast, have nearly constant latency and morphology and are generally not found in the absence of pathology. Thus, their presence is strongly suggestive of a focal or generalized neuropathy. The pathological entities most commonly associated with A-waves are polyneuropathies, particularly inflammatory neuropathies such as Guillain-Barre syndrome and lumbosacral nerve root compression.

One class of A-waves, called axon reflexes, are thought to be generated by collateral sprouting, have a simple morphology and are usually eliminated by supra-maximal stimulation. A-waves that persist with supramaximal stimulation, especially in multiple nerves, are sensitive indicators of electrophysiological abnormalities.

In the prior art, A-waves are identified using manual inspection of evoked late responses acquired during a nerve conduction study. Typically, a clinician views an ensemble of late responses in a raster format and makes a subjective determination as to whether an A-wave exists. This approach has several significant deficiencies:

(i) the subjective A-wave identification process is time-consuming and may not be performed because of time and resource limitations;

(ii) subjective A-wave identification does not support standardization of A-wave characteristics and thus may lead to wide differences in clinical results; and (iii) subjective A-wave processing is, realistically, restricted to identification of the presence or absence of an A-wave—other A-wave features that may be of diagnostic value are unlikely to be extracted in reliable manner.

SUMMARY OF THE INVENTION

In response to the deficiencies and limitations of the prior art, we have developed an automated A-wave detection algorithm which is advantageous because it:

(i) eliminates the need for the tedious, inefficient and error prone process of manual A-wave identification;

(ii) ensures consistent A-wave features, thus providing standardization of A-wave characteristics across electrodiagnostic studies—including those performed in multiple sites by different clinicians; and (iii) supports the automated extraction of a series of A-wave characteristics that maximize A-wave diagnostic utility.

In one form of the present invention, there is provided a method for detecting an A-wave, the method comprising:
  applying a series of stimuli to a nerve;
  recording a series of late responses;
  creation of a feature space map from an ensemble of late responses;
  identification of clusters within the feature space that represent A-wave components;
  consolidation of A-wave components into a discrete collection of A-waves;
  removal of false positive A-waves; and
  extraction of A-wave characteristics.

In another form of the present invention, there is provided a method for detecting an A-wave, the method comprising:
  applying a series of stimuli to a nerve;
  recording a series of evoked bioelectrical responses;
  identifying one or more attributes in each of the responses;
  utilizing each of the one or more attributes of each of the responses to create a new data set;
  creating a search window that is smaller than a the new data set;
  searching the new data set for trends by:
  sequentially applying the search window across the new data set; and
  analyzing the search window by counting the number of data points contained within the search window at each separate, sequential search window position;
  analyzing the new data set by:
  registering a positive for an A-wave component if the number of data points contained within the search window at each separate, sequential search window position exceeds a predetermined threshold; and
  registering a negative for an A-wave component if the number of data points contained within the search window at each separate, sequential search window position does not exceed a predetermined threshold; and
  consolidating the A-wave components into a single A-wave.

In another form of the present invention, there is provided a method for detecting an A-wave, the method comprising:
  applying a series of stimuli to a nerve;
  recording a series of evoked bioelectrical responses;
  identifying one or more attributes in each of the responses;
  utilizing each of the one or more attributes of each of the responses to create a new data set;
  identifying trends in the new data set; and
  analyzing the trends to identify the A-wave.

In another form of the present invention, there is provided a method for diagnosing a disorder in a patient comprising:
  detecting an A-wave in a patient by:
  applying a series of stimuli to a nerve;
  recording a series of late responses;
  creation of a feature space map from an ensemble of late responses;
  identification of clusters within the feature space map that represent A-wave components;
  consolidation of A-wave components into a discrete collection of A-waves;

removal of false positive A-waves; and extraction of A-wave characteristics; and comparing the A-wave of the patient with the A-wave of known disorder.

In another form of the present invention, there is provided a system for detecting an A-wave comprising:

a stimulation electrode;

a stimulation circuit connected to the stimulation electrode for applying a series of stimuli to a nerve;

a detection electrode;

a detection circuit connected to the detection electrode; and an analyzer connected to the detection electrode and adapted to detect an A-wave by:

recording a series of late responses detected by the detection circuit;

creation of a feature space map from an ensemble of late responses;

identification of clusters within the feature space map that represent A-wave components;

consolidation of A-wave components into a discrete collection of A-waves;

removal of false positive A-waves; and extraction of A-wave characteristics.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION THE PREFERRED EMBODIMENT

Electrical stimulation of many peripheral nerves (e.g., median, ulnar, peroneal and tibial) evokes a "late response". This response is characterized by antidromic (or retrograde) conduction of the evoked impulse from the point of stimulation to the spinal cord, reflection of the impulse in a subset of the motor neurons, and orthodromic conduction of the impulse to a location on that nerve or to the muscle(s) innervated by the nerve.

The late response may have several components, the two most commonly associated with muscle recordings are F-waves and A-waves. The F-wave represents motor neuron backfiring. The A-wave is generated by pathophysiological processes that are located distal to the motor neurons. These pathophysiological entities cause reflection or return of the antidromic impulses prior to their arrival at the motor neuron.

The present invention comprises a novel system for the automated detection of A-waves. Among other things, the novel system utilizes a unique A-wave detection algorithm which will hereinafter be discussed in detail.

More particularly, the novel A-wave detection algorithm employs a feature space representation of an ensemble of late responses to identify A-waves. The preferred embodiment of the algorithm comprises five steps:

(i) creation of a feature space map from an ensemble of late responses;

(ii) identification of clusters within the feature space that represent likely A-wave components;

(iii) consolidation of likely A-wave components into a discrete collection of likely A-waves;

(iv) removal of false positive A-waves; and (v) extraction of A-wave characteristics.

Figure 1:
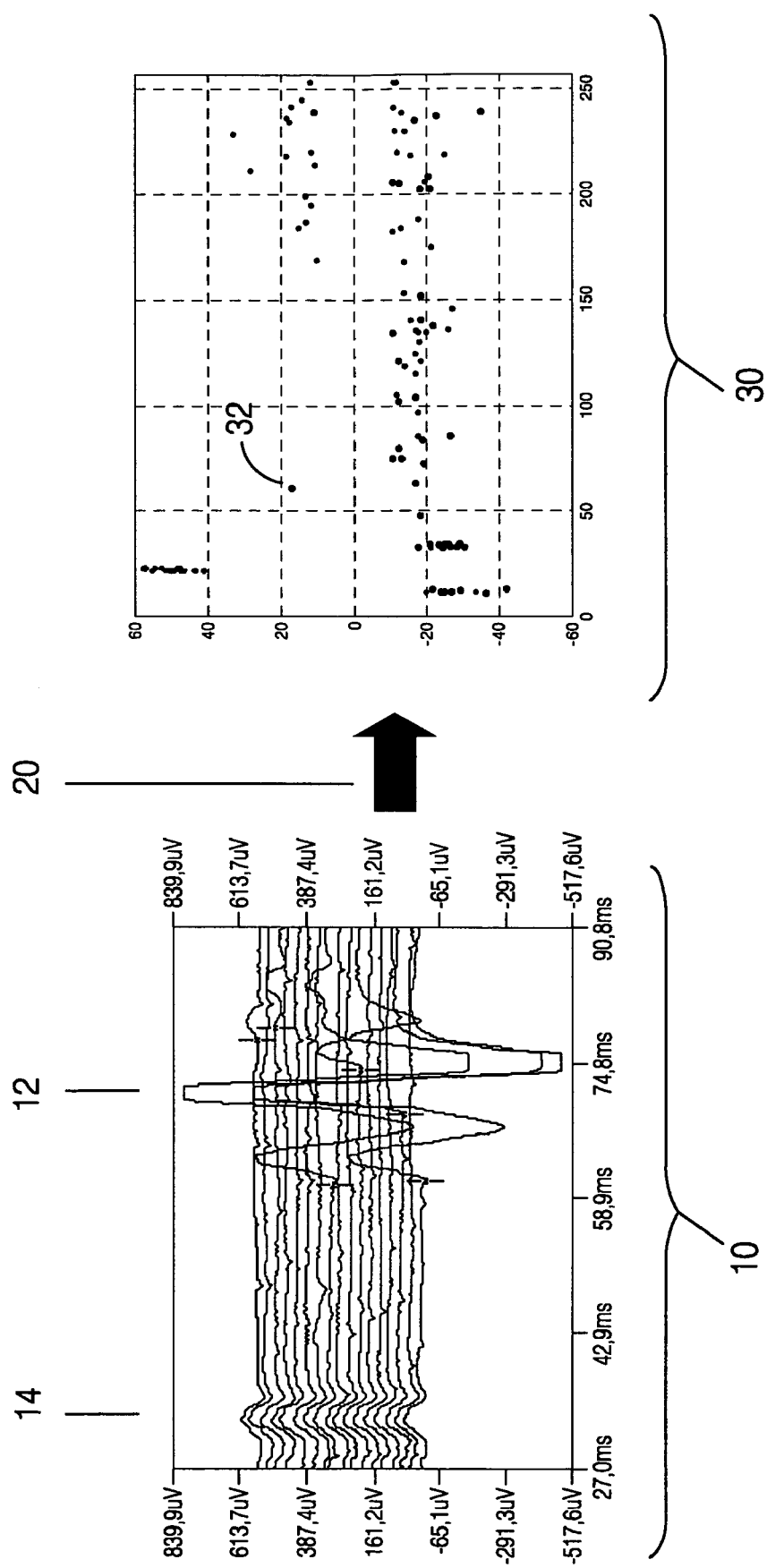
FIG. 1 is schematic drawing showing the translation of an ensemble of late response into a feature space.

In the first step, an ensemble of late responses is mapped into a feature space. The translation of an ensemble of late responses into a feature space is shown in FIG. 1. The late response traces 10 (created by a series of electrical stimuli applied to a patient's peripheral nerve, with the patient responses recorded as a series of traces by detection electrodes) may consist of F-waves 12 and A-waves 14. A translation function 20 is applied to the late responses 10, yielding a feature space map 30 consisting of discrete points 32, each of which represents one feature of one late response trace. The number of discrete points 32 within the feature space 30 can be less than, equal to, or greater than the number of late response traces 10, depending on the number of features identified per trace.

Figure 2:
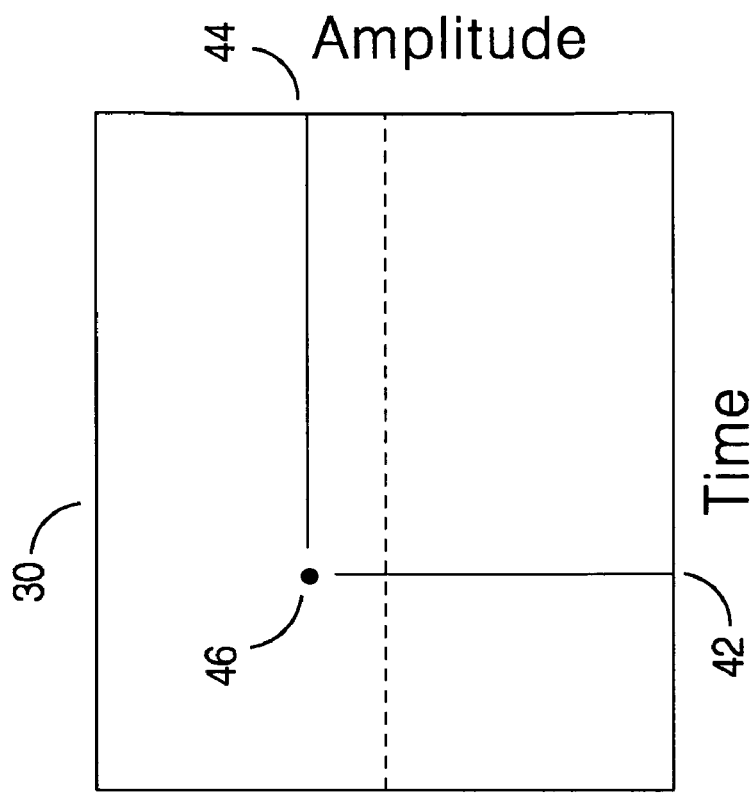
FIG. 2 is schematic drawing showing one preferred translation function for translating a feature of a late response into a feature space.
Figure 2:
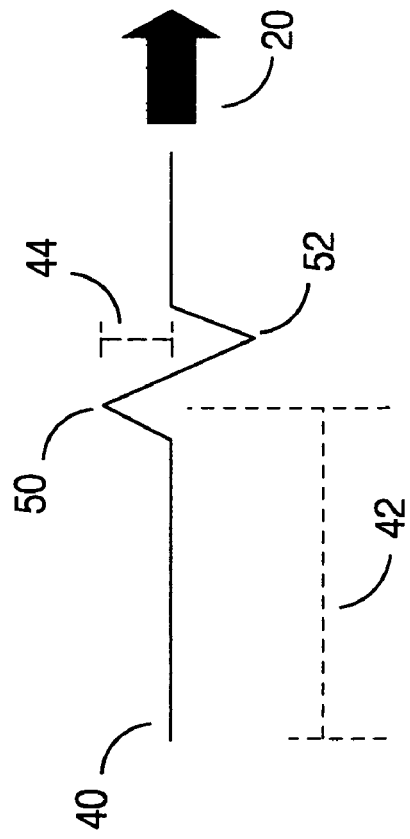

The feature space map may be created from one or more of the various features associated with the late response traces. More particularly, in the preferred embodiment of the present invention, the feature space map is created using every local maxima and local minima within each late response trace. Thus, the translation function 20 of the preferred embodiment is shown schematically in FIG. 2. The function 20 identifies every local maxima 50 and local minima 52 within each late response trace 40 (this late response trace would be one of the ensemble of traces seen in 10). A single point 46 within the feature space 30 is then created to correspond to each such maxima 50 or minima 52, whereby the location of the point 46 is determined by its time of occurrence 42 and its amplitude 44.

In additional embodiments of the present invention, other late response trace characteristics and attributes may be used to construct the feature space. By way of example but not limitation, such characteristics may include the magnitude of local maxima and local minima of various linear and non-linear translations of the response trace 40, including its first derivative, its second derivative, its absolute value, and its second power. Although, in the preferred embodiment, the attribute of the maxima or minima that is mapped into the feature space is its amplitude, other attributes could be utilized. By way of example but not limitation, such attributes include the absolute value and second power of the amplitude. In the embodiment described above, the feature space consists of two dimensions: time 42 of maxima 50 or minima 52 occurrence; and its corresponding amplitude 44. Higher dimensional feature spaces have been contemplated and should be viewed as part of the present invention. As an example, in one such embodiment, a third dimension representing the magnitude of the second derivative (i.e., "sharpness") at the time of occurrence of the maxima 50 or minima 52 is incorporated.

Figure 3:
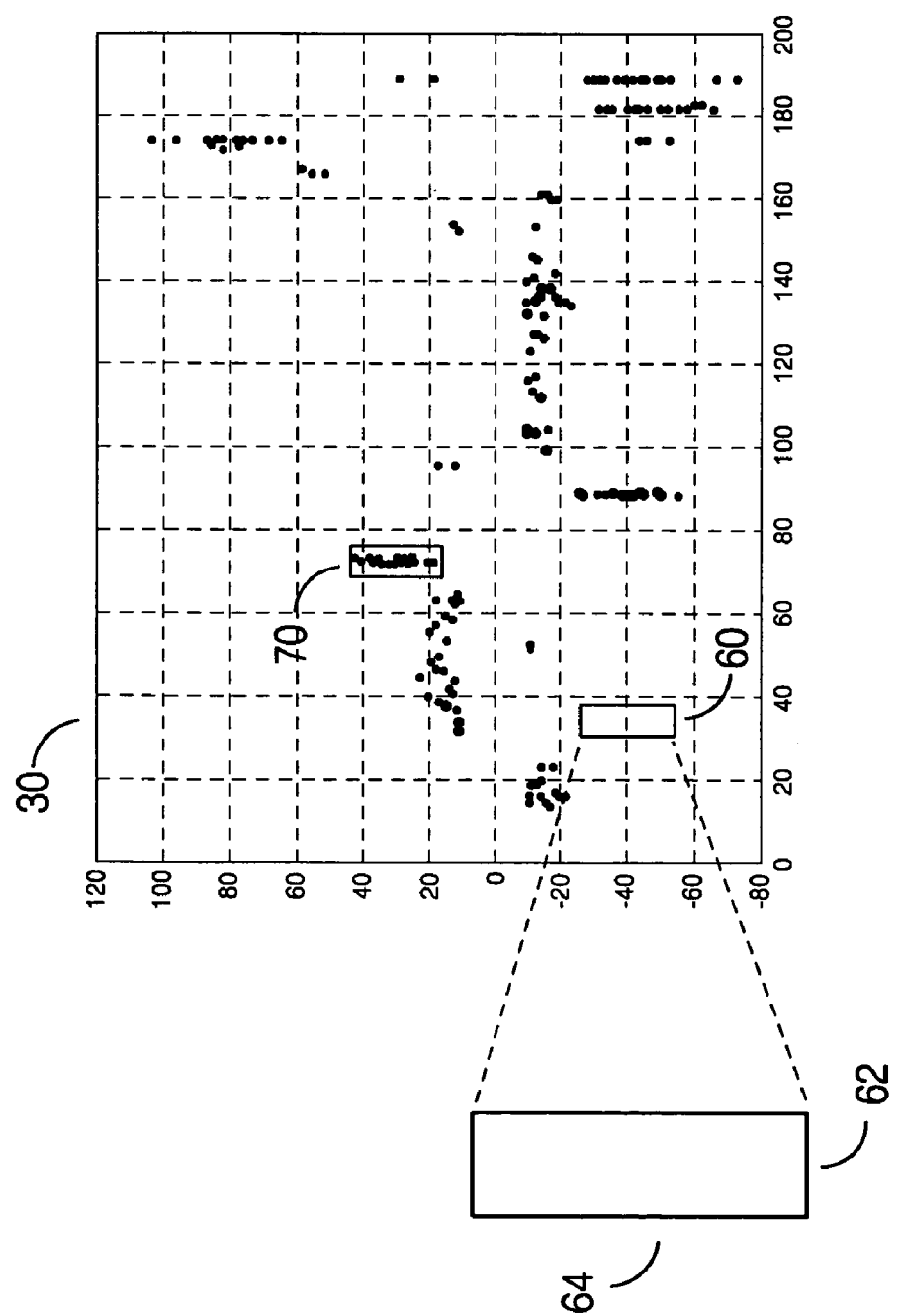
FIG. 3 is schematic drawing showing how the feature space may be searched for clusters of points that are likely to represent A-wave components.

In the second step of the preferred algorithm, the feature space is searched for clusters of points that are likely to represent A-wave components. A-waves are defined by nearly constant waveform morphology and latency. In a preferred embodiment of the algorithm shown in FIG. 3, a search window 60 of a predetermined temporal width 62 and amplitude height 64 is sequentially applied across the entire feature space 30. Any location whereby the search window overlaps at least a predetermined number of points 70 is registered as an A-wave component. In a preferred embodiment, the number of points is defined as a percentage of the number of late response traces 10. For example, the frequency of A-waves within late response ensemble 10 can vary from as low as 40% of traces to 100% of traces, and thus the search window 60 must overlap a number of points which is 40% of the number of late response traces. In another embodiment of the present invention, the search window 60 does not have to be a fixed size but can increase in either width 62 (temporal dimension) or height 64 (amplitude dimension) at different parts of the feature space. For example, as the amplitude of the features increase, there is a greater variation in the points. As a result, it is advantageous to make the height 64 of the search window 60 proportional to the amplitude location within the feature space 30.

Figure 4:
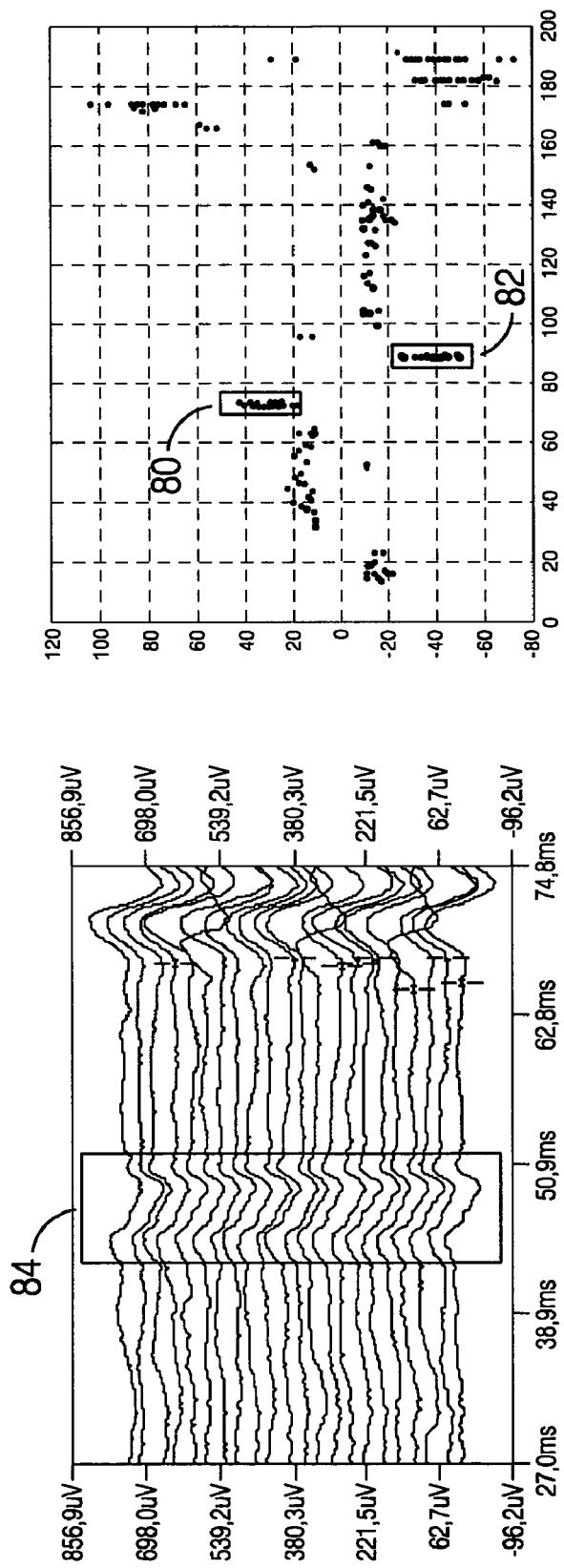
FIG. 4 is schematic drawing showing how a positive A-wave component followed a short time later by a negative A-wave component is likely to indicate two phases of the same A-wave waveform.

In the third step of the preferred algorithm, the identified A-wave components 70 are consolidated into A-waves. This is accomplished by merging A-wave components that are likely to represent different elements of the same A-wave. For example, as shown in FIG. 4, a positive A-wave component 80 followed a short time later by a negative A-wave component 82 is likely to indicate two phases of the same A-wave waveform 84. In this situation, the components are consolidated into a single A-wave.

In the fourth step of the preferred algorithm, the specificity of the ensemble of consolidated A-waves is optimized by applying a set of heuristic rules. The purpose of this step is to identify and remove "false positive" A-waves. These are segments of the late response trace that were identified as A-waves by steps 1-3 of the preferred algorithm but do not actually represent physiologically realistic A-waves. In the preferred embodiment, the rules are predetermined and include, by way of example but not limitation, minimum amplitude, minimum time of occurrence and minimum "sharpness". These rules can also be combined. For example, the minimum amplitude of an A-wave may be defined as a function of its time of occurrence, whereby A-waves that occur early in the late response must have a larger amplitude than those that occur later.

In the fifth step of the preferred algorithm, the final reduced set of A-waves is analyzed and each A-wave is characterized by a set of features. One standard feature is the amplitude of the A-wave. By way of example but not limitation, other features include the complexity of the A-wave—which may be estimated by the number of phases in the A-wave, the time of occurrence of the A-wave, the temporal dispersion of the A-wave, and the persistence of the A-wave—defined as the percentage of late response traces in which the A-wave occurs.

The presence or absence of A-waves in a late response ensemble, as well as the characteristics of these A-waves, can be used as is known in the art to diagnose neuropathic conditions. For example, the presence of an A-wave in the peroneal nerve is suggestive of a chronic lesion of the L5 nerve root, otherwise known as sciatica. As another example, the presence of A-waves in multiple nerves of a diabetic individual is indicative of diabetic polyneuropathy. As yet another example, the occurrence of complex A-waves in a patient presenting with rapid onset proximal weakness is the earliest sign of Guillan-Barre syndrome.

What is claimed is:

1. A method for detecting an A-wave, the method comprising:
    applying a series of stimuli to a nerve;
    recording a series of evoked bioelectrical responses;
    identifying one or more attributes in each of the responses;
    utilizing each of the one or more attributes of each of the responses to create a new data set;
    creating a search window that is smaller than the new data set;
    searching the new data set for trends by:
        sequentially applying the search window across the new data set; and
        analyzing the search window by counting the number of data points contained within the search window at each separate, sequential search window position;
    analyzing the new data set by:
        registering a positive for an A-wave component if the number of data points contained within the search window at each separate, sequential search window position exceeds a predetermined threshold; and
        registering a negative for an A-wave component if the number of data points contained within the search window at each separate, sequential search window position does not exceed a predetermined threshold; and
    consolidating the A-wave components into a single A-wave.

2. A method according to claim 1 wherein the search window has an area such that the height of the search window is proportional to the amplitude location within the new data set.

3. A method according to claim 1 wherein the one or more attributes comprise the amplitude of local maxima and/or local minima.

4. A method according to claim 1 wherein the one or more attributes comprise the absolute value amplitude.

5. A method according to claim 1 wherein the one or more attributes comprise the second derivative of amplitude.

* * * * *